United States Patent [19]

Chow et al.

[11] Patent Number: 5,397,350
[45] Date of Patent: Mar. 14, 1995

[54] INDEPENDENT PHOTOELECTRIC ARTIFICIAL RETINA DEVICE AND METHOD OF USING SAME

[76] Inventors: Alan Y. Chow, 191 Palomino Pl., Wheaton, Ill. 60187; Vincent Chow, 7980 Kingsbury Dr., Hanover Park, Ill. 60103

[21] Appl. No.: 56,672

[22] Filed: May 3, 1993

[51] Int. Cl.[6] .................. A61N 1/00; A61F 2/14; A61B 17/00
[52] U.S. Cl. ..................... 623/4; 128/898; 607/53; 607/116
[58] Field of Search ............ 607/115, 116, 53, 54; 128/898; 623/4, 24, 66

[56] References Cited

U.S. PATENT DOCUMENTS

| | | | |
|---|---|---|---|
| 2,760,483 | 10/1954 | Tassicker | 623/4 X |
| 3,594,823 | 7/1971 | Collins | 623/66 X |
| 3,628,193 | 12/1971 | Collins . | |
| 3,766,311 | 10/1973 | Boll | 623/66 X |
| 3,848,608 | 11/1974 | Leonard . | |
| 3,914,800 | 10/1975 | Collins | 623/66 X |
| 4,251,887 | 2/1981 | Anis | 606/107 X |
| 4,272,910 | 6/1981 | Danz | 623/4 X |
| 4,551,149 | 11/1985 | Sciarra | 623/4 |
| 4,600,004 | 7/1986 | Lopez et al. | 606/1 |
| 4,601,545 | 7/1986 | Kern | 623/4 X |
| 4,628,933 | 12/1986 | Michelson . | |
| 4,750,498 | 6/1988 | Graham | 606/107 X |
| 4,836,202 | 6/1989 | Krasner | 606/107 |
| 5,016,633 | 5/1991 | Chow . | |
| 5,024,223 | 6/1991 | Chow . | |
| 5,109,844 | 5/1992 | de Juan, Jr. et al. | 607/53 |

OTHER PUBLICATIONS

"Artificial Vision: A Big Step Forward" *Science News*, Feb. 2, 1974, vol. 105, No. 5, p. 105.
*Science*, Jul., 1981.

Primary Examiner—Randall L. Green
Assistant Examiner—Mary Beth O. Jones
Attorney, Agent, or Firm—Willian Brinks Hofer Gilson & Lione

[57] ABSTRACT

Microscopic photoelectric devices with semitransparent surface electrodes are combined with a liquid or other suitable vehicle. Together they are injected into the subretinal space of the eye. The microscopic photoelectric devices transduce incident light into electric current that will stimulate the overlying cellular layers of the retina. In persons suffering from visual disfunction due to outer retinal layer damage, such devices may allow useful formed artificial vision. The preferred independent surface electrode microphotodiodes (ISEMCP's) may be in the shape of microspheres, microdiscs or other microshapes. The ISEMCP's are formed of either PiN or NiP type semiconductors, or a combination of both, in a single unit. These devices will form a dipole when exposed to light due to the electric current generated. A magnetic field applied in the vicinity of the eye may help align the ISEMCP's within the retina so that their photo-active surfaces face the incident light. Alternatively, the ISEMCP's may be embedded and prealigned in a transparent flexible sheet, permeable to nutrients and oxygen, before implantation into the subretinal space. Such sheet will allow passage of biological nutrients and oxygen around the ISEMCP's. This sheet may also dissolve leaving behind ISEMCP units lying separately, or in an arranged pattern produced by a surrounding mesh.

18 Claims, 10 Drawing Sheets

INDEPENDENT PHOTOELECTRIC ARTIFICIAL RETINA DEVICE AND METHOD OF USING SAME

BACKGROUND OF THE INVENTION

The present invention is directed to a medical product which can be used to correct vision loss or blindness caused by certain retinal diseases. A variety of retinal diseases cause vision loss or blindness by destruction of the choroid, choriocapillaris, and the outer retinal layers of Bruch's membrane and retinal pigment epithelium. Loss of these layers is followed by degeneration of the inner retinal photoreceptor layer. As severe as the disruption of the outer retina usually is, the remaining inner retina (composed of the outer nuclear, outer plexiform, inner nuclear, inner plexiform, ganglion cell and nerve fiber layers) may be spared. The sparred inner retina can be utilized, in combination with devices that perform the function of the damaged photoreceptor cells, to restore vision.

Prior efforts to produce vision by stimulating various portions of the retina have been reported. One such attempt involved an externally powered, but internally located, photosensitive device with opposing photoactive and electrode surfaces. The device would theoretically stimulate the nerve fiber layer by its direct placement upon this layer from the vitreous body. The success of this device is questionable, however, due to the complex frequency modulated neural signals of the nerve fiber layer that the device must duplicate. Further, the normal nerve fiber layer runs in a general radial course with many layers of overlapping fibers appearing from different portions of the retina. Selection of the appropriate nerve fibers to stimulate in order to produce formed vision, therefore, would be extremely difficult, if not impossible.

Another prior device involved a unit consisting of a supporting base onto which a photosensitive material such as selenium was coated. This device was designed to be inserted through an external scleral incision made at the posterior pole of the eye. The device would rest between the sclera and choroid, or between the choroid and retina. Light would cause a potential to develop across the photosensitive surface producing ions that would theoretically migrate into the retina causing stimulation. However, having no discrete surface structure to restrict the directional flow of charges, lateral migration and diffusion of charges would occur thereby preventing sufficient image resolution to be developed. One such device was reportedly constructed and implanted into a patient's eye resulting in light perception, but not formed imagery.

Placement of this device between the sclera and choroid would also result in blockage of discrete ion migration to the photoreceptor and inner retinal layers. This effect is due to the intervening presence of the choroid, choriocapillaris, Bruch's membrane and the retinal pigment epithelial layer—all of which would block passage of these ions. Placement of the device between the choroid and the retina would still interpose Bruch's membrane and the retinal pigment epithelial layer in the pathway of discrete ion migration. As this device would be inserted into or through the highly vascular choroid of the posterior pole, subchoroidal, intraretinal and intraorbital hemorrhaging would likely result along with disruption of blood flow to the posterior pole.

U.S. Pat. Nos. 5,016,633 and 5,024,223, both issued to the present inventor (the contents of which are hereby incorporated by reference), also reported a design for a subretinally placed photoelectric device comprised of multiple surface electrode microphotodiodes (SEMCP's) deposited on a single silicon crystal substrate. These SEMCP's transduce light, passing through a semitransparent electrode surface and onto a photoactive surface, into small electric currents that stimulate overlying and surrounding inner retinal cells. However, due to the solid nature of the substrate onto which the SEMCP's were placed, blockage of nutrients from the choroid to the inner retina likewise occurs. Even with fenestrations of various geometries, permeation of oxygen and biological substances is not optimal.

SUMMARY OF TEE INVENTION

In view of the above, the current invention provides, in one aspect, a photoelectric device for insertion into the retina of a mammal suffering from vision loss as a result of damage to the choroid, choriocapillaris and/or the outer retinal layers of Bruch's membrane and retinal pigment epithelium. In one preferred embodiment of the invention, such device comprises a plurality of separate independent surface electrode microphotodiodes (ISEMCP's), which are placed in a liquid or other suitable solution. Individual ISEMCP's may assume various shapes including, but not limited to, microspheres and microdiscs that transduce light passing through their semitransparent electrode surfaces. The output of each discrete ISEMCP that receives incidental light produces an electrical signal that simulates the effects on photoreceptors and bipolar cells, similar to that created by the damaged retina cells, to produce formed images.

According to another aspect of the invention, a method is provided for depositing a plurality of these discrete ISEMCP's, spaced apart from each other, into the subretinal space of the eye. The ISEMCP's may be implanted by injection into the subretinal space of the eye preferably through a pars plana vitreous and retinotomy approach. The ISEMCP's may also be disposed in a sheet of dissolvable or non-dissolvable material, which is implanted by direct placement into the subretinal space of the eye. Upon exposure to images formed by incident light, a small electric current is generated by the individual ISEMCP's, which stimulate the overlying inner retinal cells in a pattern resembling the formed image.

When inserted subretinally into the space between the inner and outer retinal layers, an amplitude modulated electric current is produced by each ISEMCP when incident light passes through its semitransparent front electrode surface. The amplitude of this current, varying directly with the intensity of illumination, will depolarize and/or hyperpolarize the overlying inner retinal layer. This layer consists of photoreceptors, bipolar cells and horizontal cells. As these cells normally both receive and produce analog amplitude modulated currents, the similarly modulated output of the ISEMCP's is a well suited substitute for stimulation of these cells.

The amplitude modulated signal of healthy bipolar cells is then modified and converted by the amacrine and ganglion cells to a frequency modulated signal following the normal biological mechanisms of the inner retina. The final action potential is transmitted through the optic nerve to the brain. Because the complex conversion of amplitude modulated signals to frequency modulated signals is left to intrinsic retinal mechanisms, formed vision with subretinally implanted ISEMCP's is greater than in devices that attempt to stimulate the nerve fiber layer directly with electronically constructed, frequency modulated signals, The artificial retina device of this invention therefore is composed of multiple ISEMCP's disposed in the subretinal space of the eye. From the injection of ISEMCP's, alignment may be random, in which case only those ISEMCP's with favorable alignment towards incident light will produce electric current. Those ISEMCP's not aligned are inert and do not adversely impact operation of the properly aligned receptors. A sufficient number of ISEMCP's are preferably deposited to increase the percentage of those devices that are beneficially aligned. To further ensure such alignment, the ISEMCP's may be ordered by application of an external magnetic field at or near the eye.

As mentioned, ISEMCP's may also be embedded into a transparent flexible substance for implantation into the subretinal space. This substance may be fabricated from non-dissolvable hydrophilic and nutrient-permeable substances such as that used to fashion soft contact lenses. Alternatively, the substance may be made from dissolvable substances such as agar or collagen. A fine mesh made of an inert substance such as nylon or polypropylene may also surround the individual ISEMCP's producing a patterned or regular arrangement of the units.

The device and method of this invention represents a significant improvement over the SEMCP concept of the prior art. The open spaces between the individual ISEMCP's, as they settle into a monolayer in the subretinal space, allow improved biological nutrients and oxygen to flow between the outer and inner retinal layers. Further, because the subretinal areas designated for implantation of the ISEMCP's can be accurately selected by the injection process used to implant these units, irregular areas of outer retinal dysfunction are readily treatable.

These and other features and advantages of the invention will be further understood to those skilled in the art upon consideration of the following detailed description of the presently preferred embodiments of the invention, taken in conjunction with the appended drawings.

DETAILED DESCRIPTION OF THE PRESENTLY PREFERRED EMBODIMENTS

Figure 1:
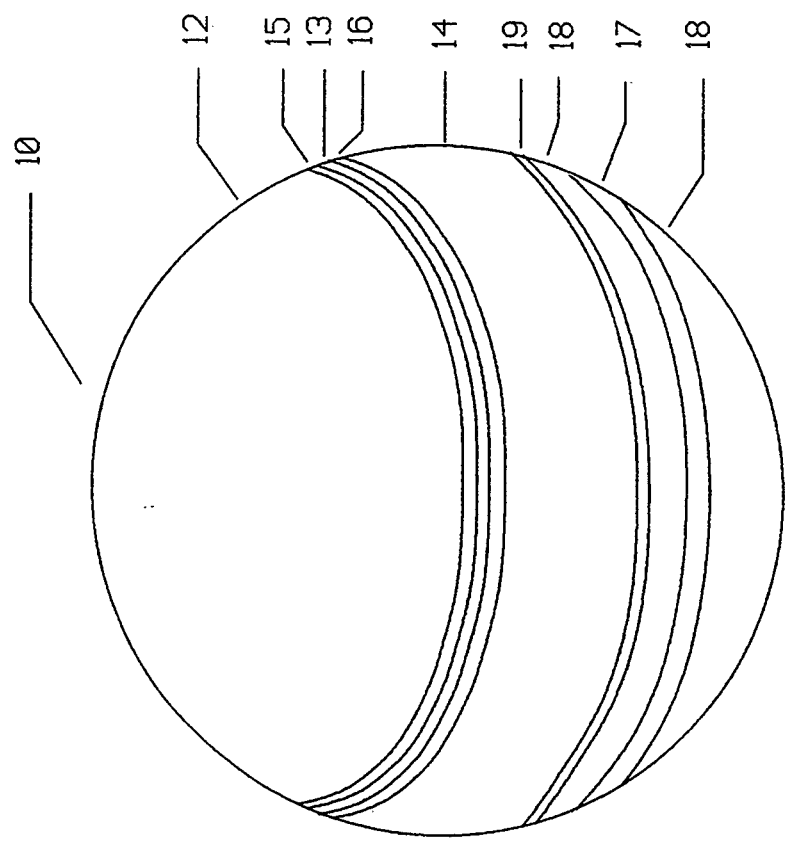
FIG. 1 is a perspective view of a single ISEMCP microsphere unit showing its layered architecture.

Referring first to FIG. 1, the surface microarchitecture of one presently preferred embodiment of the photoelectric device of the invention is generally designated at 10. In the preferred embodiment, such photoelectric device comprises the ISEMCP discussed above, although those skilled in the art will appreciate that other photoelectric devices can be employed without departing from the spirit and scope of the invention. As shown in FIG. 1, the preferred ISEMCP 10 forms a spherical shape and is sized in microscopic dimensions.

In its basic form, the ISEMCP 10 contains a semitransparent surface electrode 12. The surface electrode 12 is preferably made of polysilicon created by standard ion implantation, thermal diffusion or chemical vapor deposition techniques. Alternatively, the surface electrode 12 may be constructed of any suitable material that will conduct electric current and allow light to pass through it. Thus, the surface electrode 12 may also be made of a thin, semitransparent layer of gold, which has been vacuum deposited over a thin semitransparent layer of chromium. (Chromium is used to improve adhesion of the gold layer to the other layers described below.) Other conductive materials which can be used instead of gold include aluminum and platinum.

As shown in FIG. 1, the surface electrode 12 forms the positive electrode of a semiconductor photodiode, which is formed at the P junction 13 between the surface electrode 12 and a negatively doped substrate 14. Between the surface electrode 12 and the junction 13 is an enhanced polysilicon (P+) layer 15, which allows good electrical contact between the electrode and the junction 13. The P junction 13 also contacts one side of an intrinsic (i) layer 16, which occurs naturally in the manufacture of the microphotodiode. On the opposite side of the intrinsic layer 16 is the negatively doped bulk silicon substrate 14.

The P junction 13 and the negatively doped substrate 14, therefore, form the P-N halves of the semiconductor photodiode included in each ISEMCP 10. Behind the doped substrate layer 14, however, are several more layers, including an optional layer of magnetically susceptible material 17 (described below), negatively doped polysilicon layers 18, and an enhanced conductive N+ layer 19 where the doped substrate 14 contacts the negative polysilicon (N) layer 18.

In the preferred embodiment of the invention, the diameter of an ISEMCP is between 1 to 25 microns. However, in alternate embodiments, the ISEMCP may be manufactured as small as 0.1 micron or as large as 1000 microns without departing from the spirit and scope of the invention. Similarly, in the preferred embodiment, each ISEMCP has a high ohmic (resistive) value with resistances between 1 ohm/cm and 50,000 ohm/cm. As those skilled in the art will also appreciate, the above-described, preferred ISEMCP 10 has been shown in a P-i-N configuration of semitransparent surface electrodes, but an N-i-P silicon microphotodiode may also be readily manufactured and is thus equivalent to the preferred ISEMCP 10.

Figure 2:
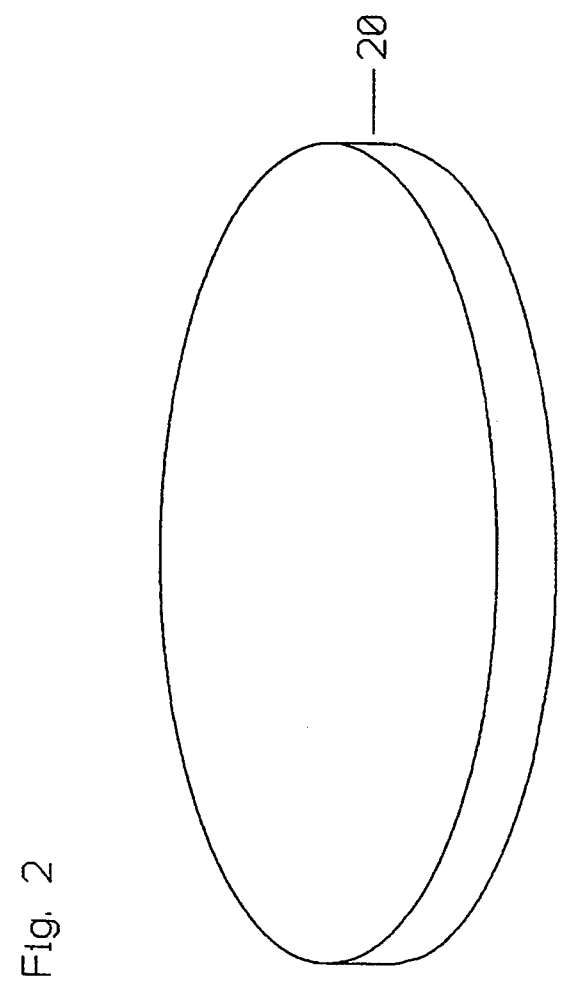
FIG. 2 is a perspective view of a silicon wafer used in the manufacture of the preferred ISEMCP's of the invention.
Figure 3:
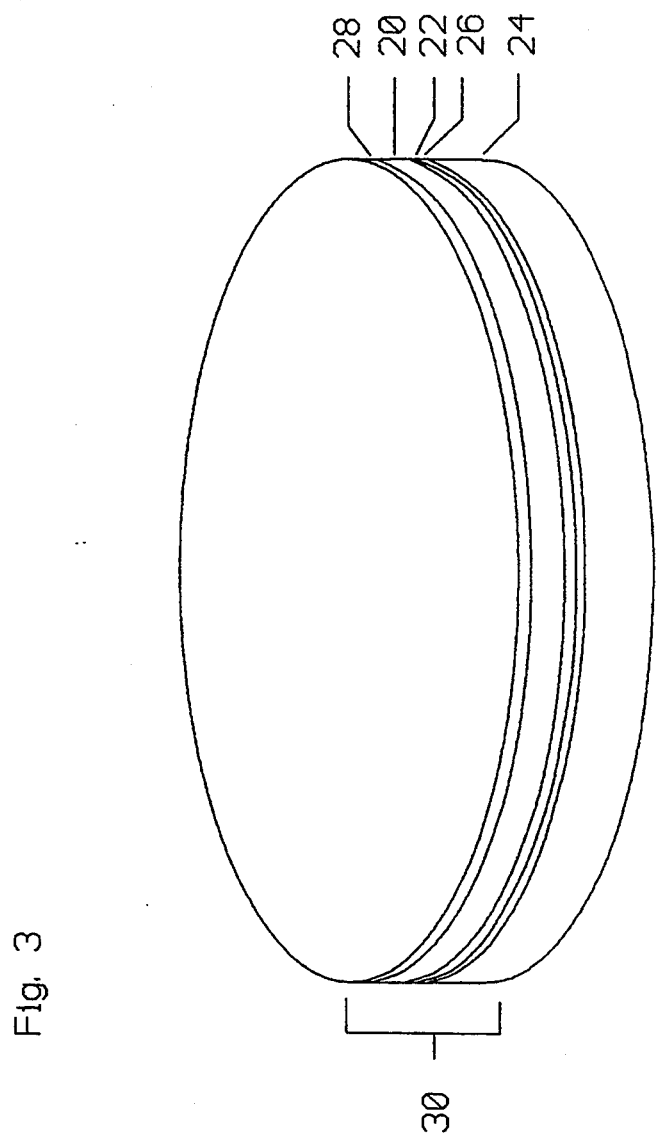
FIG. 3 is a perspective view of the materials added to the silicon wafer of FIG. 2 in the manufacture of the ISEMCP's.
Figure 4:
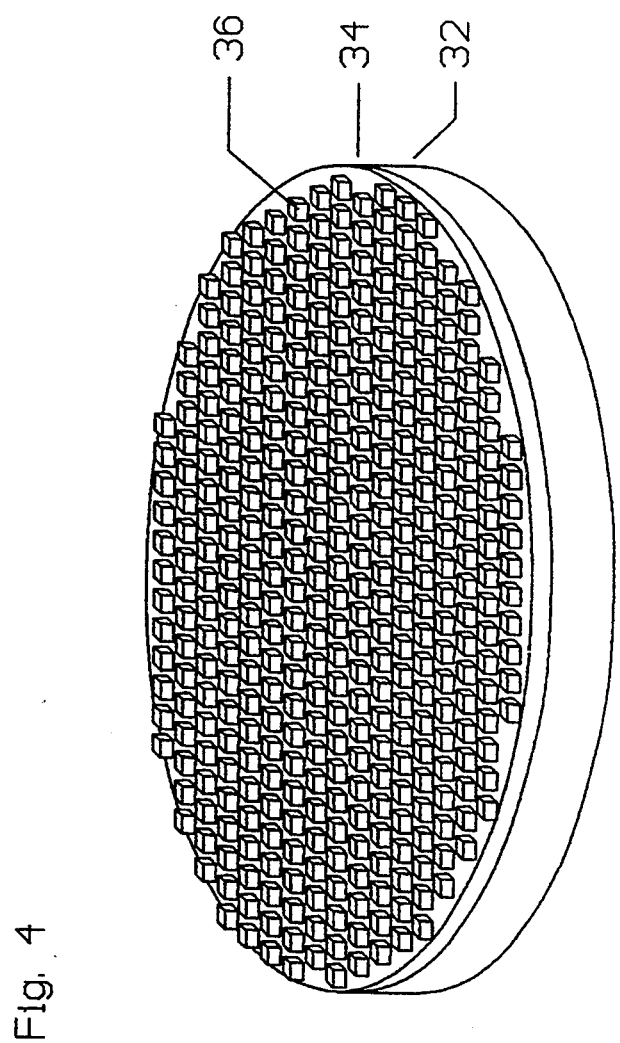
FIG. 4 is a perspective view of plural ISEMCP microcubes prior to lapping.

A typical manufacturing process for the preferred P-i-N ISEMCP 10 microsphere shown in FIG. 1, having dimensions of approximately 25 microns, is shown in FIGS. 2–4. Referring to FIG. 2, the first stage in the manufacture of such ISEMCP's includes mechanically lapping a basic three inch diameter N-doped silicon wafer 20 from a typical manufactured thickness of 21 mils to an ultra-thin starting thickness of five mils. This preferred starting thickness allows sufficient mechanical strength for further processing, which is described below. By starting with a thin wafers moreover, the complexity of these subsequent steps is substantially reduced.

With standard ion implantation, thermal diffusion or chemical vapor deposition techniques, the bottom surface of the wafer 20 is converted into a single region P-junction semiconductor, as shown in FIG. 3. Preferably, seven microns of P-doped polysilicon is added to the wafer 20 as the P anode, which forms part of the P layers 22. The P layers 22 include layers 12, 13 and 15 of the preferred ISEMCP shown in FIG. 1. The P layers 22 also include the intrinsic layer 16, which is created after P junction 13 ion implantation.

The bottom side of the wafer 20 (the P-doped polysilicon side) is then affixed to a ceramic disk 24 with a chemically soluble non-aqueous adhesive 26. As those skilled in the art will appreciate, this technique is similar to that used in mirror grinding and failure analysis cross-sectioning. With the increased mechanical strength afforded by the ceramic disk 24, the topside of the wafer 20 is again lapped mechanically to a thickness of two mils. At this stage of the manufacturing process it is also preferable to ensure that the front and back surfaces of the wafer 20 are parallel. Final thinning of the silicon wafer 20 is accomplished by standard chemical etch. A target thickness of 11 microns for the non-polysilicon portion is thus achieved.

A shallow N+ layer 28 is then implanted on the top of the negatively doped substrate 20. The N+ layer is deposited using standard ion implantation techniques generally known in the art. Next, a seven micron N-doped polysilicon layer is laid down, which serves as the N cathode electrode 18 shown in FIG. 1. The N-doped polysilicon layer is deposited using chemical vapor deposition techniques, also generally known to those skilled in the art.

When complete, the final structure is preferably 25 microns thick: seven microns of P poly 22, 11 microns of silicon bulk 20, and seven microns N poly 28 (with the intrinsic layer 16 (FIG. 1) being formed between the P-poly 22 and the bulk 20 layers).

The final wafer assembly 30 is then laser sliced along the X direction to produce strips of silicon 25 microns wide. Because of the small dimensions of the cut, excimer laser slicing is preferred. Lateral damage into the silicon by the excimer laser is less than one micron. The assembly 30 is then laminated onto a second ceramic disk 32 (similar to the first piece) whose function is to hold all silicon slices in place when the wafer is again laser cut in the Y direction. Unlike the adhesive 26 of FIG. 3, the aqueous adhesive 34 used in this step is preferably not dissolvable in the solvent used in the next step. Thus, the assembly 30 is placed in a nonaqueous solvent that dissolves the first adhesive, but not the second.

The assembly 30 is laser cut along the Y direction with the same pitch as previously employed in the X direction. When completed, the wafer 20 will have been converted into a plurality of microcubes 36 (FIG. 4), each of which is 25 microns on a side. The assembly 30 is finally placed into a second aqueous solvent to dissolve the remaining adhesive 34. When the second adhesive layer 34 is dissolved, the silicon microbes 36 remain suspended in the solvent. The bulk ceramic disk base 32 is then removed from the solution, leaving only the suspended silicon microcubes 36. The silicon microcubes 36 are then recovered and placed in a water suspension. As those skilled in the art will realize, the fabrication of N-i-P devices is similar to the above process except with the reversal of the P and N stages.

Depending on the desired shape of the ISEMCP's chosen, a certain amount of polishing is then performed on the silicon microcubes 36. To polish the silicon microcubes 36, the water suspension of microcubes 36 is placed between two circular glass lapping plates (not shown) in a manner generally known in the art. These plates are capacitively monitored and time/pressure controlled to provide a very precise polishing action. With this approach, the cubic silicon structures 36 are polished into smooth silicon microspheres 10 (shown in FIG. 1) with precise and consistent diameters. When lapping is completed, the silicon ISEMCP microspheres 10 are washed, recovered, sterilized and placed in a physiologically compatible semi-solid or liquid vehicle ready for injection or implantation into the eye.

Referring again to FIG. 1, because the P region 13 governs the active junction depletion zone where photon conversion occurs, only microspheres with the P surface electrode 12 facing incident light will respond by producing a photoelectric current. The designed and preferred electric current output of each ISEMCP 10 is on the order of one to 250 nA in average room or ambient lighting. Nevertheless, a range of 0.01 nA to 10,000 nA is also suitable. The ISEMCP's 10 may also be modified to achieve a greater or smaller output, depending upon the stimulation requirements of the overlying cell layer, by changing the size of the ISEMCP's 10 and/or the thickness of the semitransparent surface electrodes 12 and 18. As the amplitude of the output of each ISEMCP 10 is modulated by the intensity of the incident light, its effect on the inner retina and bipolar cells will be similar to the photoreceptors at this initial site. It may also preserve the on-off receptor fields function providing contrast recognition in addition to producing formed images.

Figure 5:
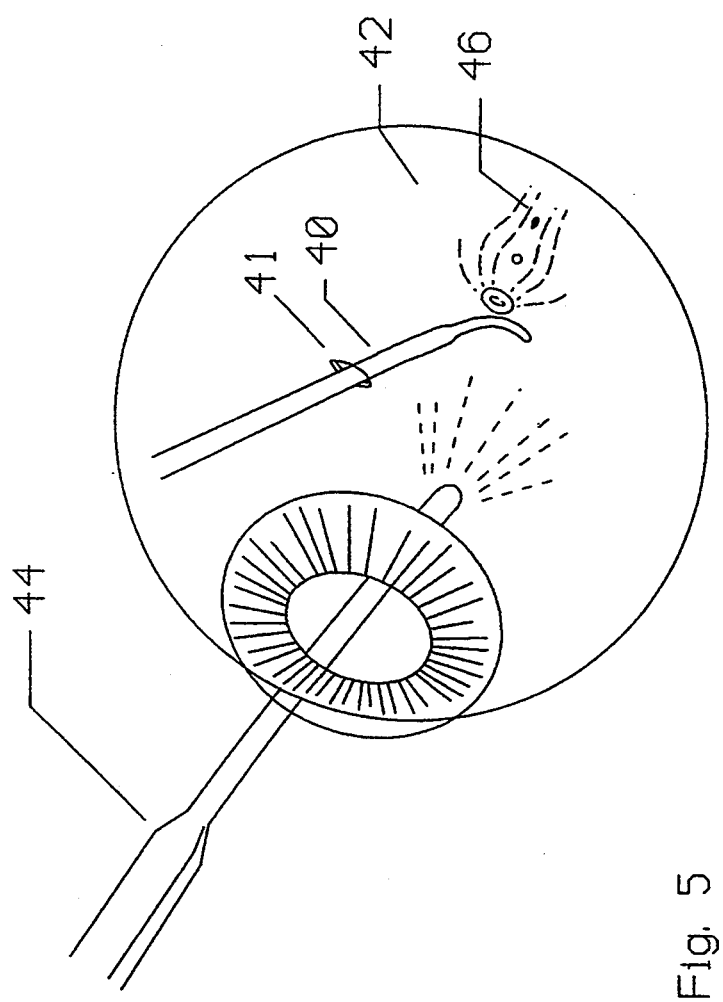
FIG. 5 illustrates a canula being inserted into the subretinal space ready for subretinal injection and implantation of the ISEMCP's.

As illustrated in FIG. 5, the photoelectric device of this invention is preferably implanted into the subretinal space by injection with a very fine canula 40. Preferably, the ISEMCP's are placed in a vehicle such as (but not limited to) a liquid, and injected into the subretinal space via a retinotomy incision 46 using the canula 40. Such a liquid vehicle may be a balanced salt solution or a more viscous material like methylcellulose. A viscous vehicle will allow more even suspension of the ISEMCP's than the balanced salt solution. Other vehicles include oxygen and nutrient permeable semi-solid solutions.

The retina 42 is preferably illuminated by a light pipe 44 to facilitate the injection of the ISEMCP'so As shown in FIG. 5, the canula 40 is introduced into the vitreous cavity of the eye via a pars plana incision 41. Dissection of the posterior vitreous is performed to separate the posterior hyaloid face from the retinal surface. A small retinotomy incision 46 is made through the retina following the direction of the nerve fiber layer using a stiletto type MVR blade. Dissection of the inner retina from the outer retinal layers is accomplished mechanically with the canula 40.

Figure 6:
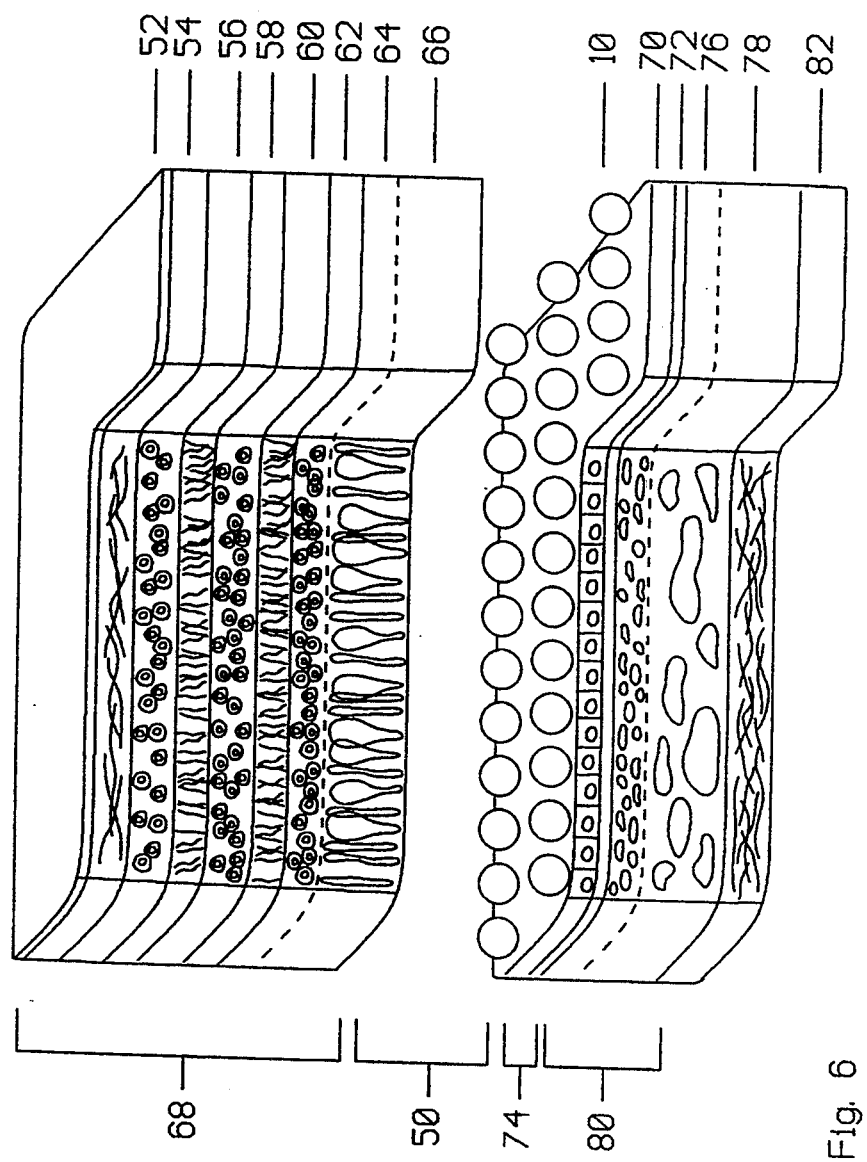
FIG. 6 is an exploded cross-sectional view of a portion of the retina illustrating plural ISEMCP's in their preferred location in the subretinal space between the inner and outer retinal layers.

When the appropriate retinal areas to receive the implantation have been prepared with canula dissection, the liquid vehicle with suspended ISEMCP's is injected. An attempt should be made to distribute the suspended ISEMCP's 10 in a uniform monolayer, as shown in FIG. 6. The canula 40 is then withdrawn and a heavier-than-water non-miscible material. (preferably, a perfluorocarbon) is placed over the posterior pole of the vitreous cavity to aid in settling of the retina. The non-miscible material is preferably removed after an appropriate time, usually 15 to 20 minutes, leaving a reattached retina. With settling and reattachment of the retina, the implanted ISEMCP's 10 will tend to become distributed into the desired monolayer.

Figure 8:
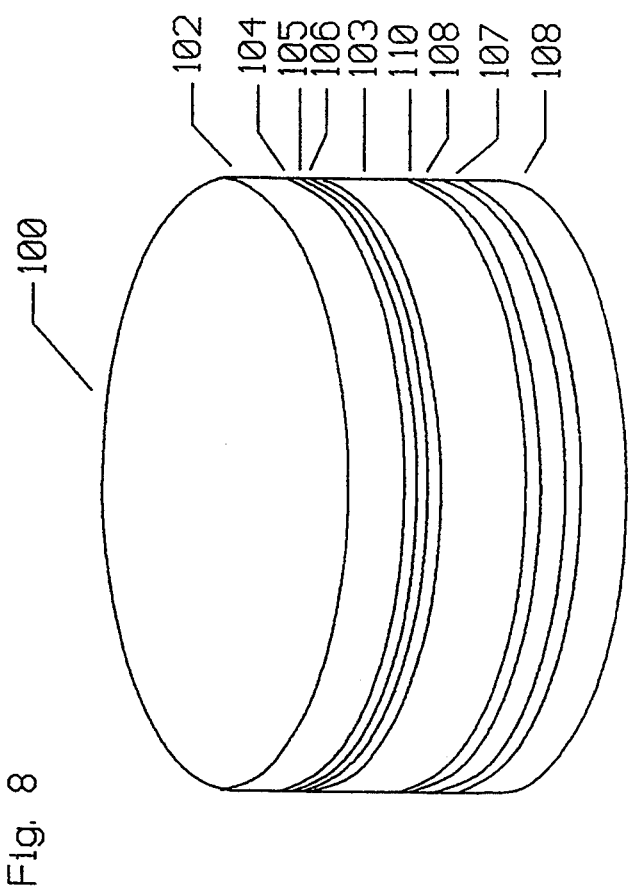
FIG. 8 is a perspective view of a single ISEMCP microdisc unit showing the layered architecture shown in FIG. 1.

In FIG. 6, the ISEMCP's 10 are shown in their preferred monolayer position in the subretinal space 50. The layers of the eye at the posterior pole from inside to outside are also shown in FIG. 8 in their respective positions: internal limiting membrane 52; nerve fiber layer 54; ganglion and amacrine cell layer 56; inner plexiform 58; inner nuclear layer 60; outer plexiform 62; outer nuclear and bipolar cell layer 64; and photoreceptor layer 66, all of which constitute the inner retinal layer 68. The ISEMCP's 10 are thus disposed between the inner retinal layer 68, and retinal pigment epithelium 70 and Bruch's membrane 72, which constitute the outer retinal layer 74. External to the retina, choriocapillaris 76 and choroid 78 comprise the choroidal vasculature 80 and sclera 82, the outer coat of the eye.

Figure 7:
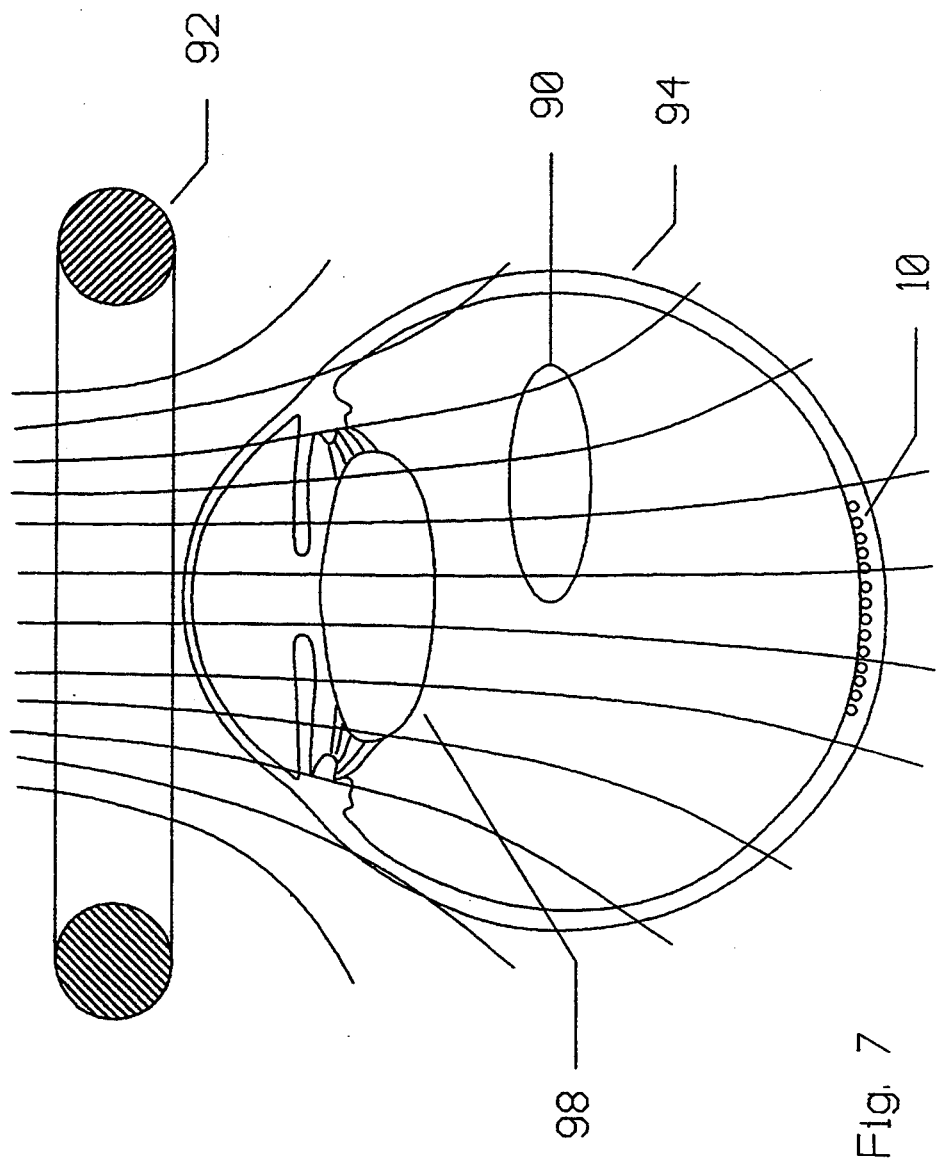
FIG. 7 illustrates a magnetic field produced by an electromagnetic coil directing alignment of ISEMCP's implanted in the subretinal space.

Referring next to FIG. 7, the ISEMCP's 10 may be aligned after insertion by use of a magnetic field 90 produced by an electromagnetic coil 92 or the like placed in the vicinity of the eye 94. As many of the ISEMCP's 10 as possible should be oriented so that the P-doped layer 15 (FIG. 1) is oriented to receive incident light through the lens 98 of the eye 94 (FIG. 7). Magnetic field lines 90 shown in FIG. 7 will interact with the dipole characteristics of the ISEMCP's 10 and produce appropriate alignment of the majority of the ISEMCP's 10, similar to the behavior of iron filings near a magnet. The ISEMCP's 10 have innate dipole characteristics when photo-stimulated, so magnetic orientation should be performed while the ISEMCP's 10 are illuminated. Alternatively, the ISEMCP's 10 can be embedded with substances (preferably, nickel, cobalt, samarium, palladium, or magnetically susceptible ceramics) that have strong magnetic susceptibility (FIG. 1) to assist in obtaining such beneficial alignment. As shown in FIG. 1, these magnetically susceptible substances 17 are preferably disposed within the N polysilicon electrode on the rear of the ISEMCP's 10. In manufacture, these substances are deposited partway into the N polysilicon deposition phase, and are preferably vacuum deposited.

As mentioned above, the ISEMCP's may take on other microscopic structures without departing from the spirit and essential scope of the invention. For example, as shown in FIG. 8, another embodiment of the ISEMCP 100 may be as a microdisc structure with semitransparent surface electrodes 102 and 108, P+ layer 104, P junction layer 105, intrinsic layer 106, N substrate layer 103, N+ layer 110, N-polysilicon layer 108 and magnetically susceptible material layer 107.

The microdisc ISEMCP's 100 shown in FIG. 8 are preferably manufactured to diameters on the order of one micron to 2000 microns. These units are fabricated similarly to the microspheres shown and described above in connection with FIG. 1, with the exception that their larger size results from a larger original dicing specification. Additionally, the microdisc ISEMCP's 100 are lapped a shorter time than the micro-sphere ISEMCP 10 units in order to preserve their cylindrical shape, but sufficient to round the corners of the microcubes to a smooth circular finish.

Figure 9:
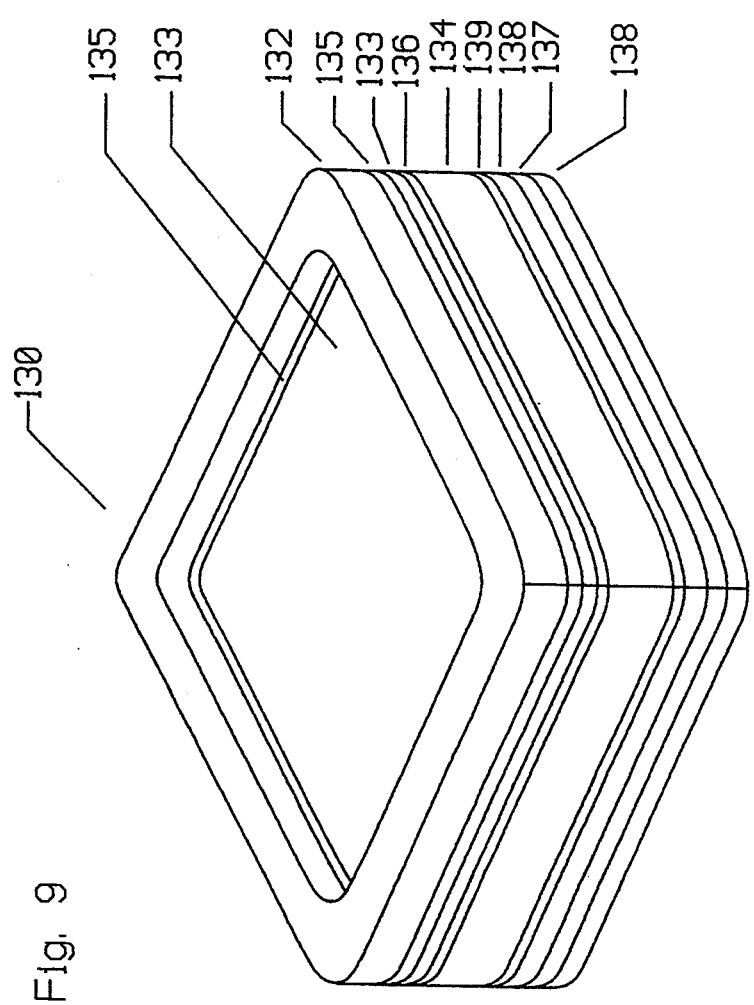
FIG. 9 is also a perspective view of an ISEMCP microdisc where the front surface electrode covers only a fraction of the photo-active surface.

Alternatively, another embodiment of the ISEMCP devices of the invention is shown in FIG. 9. In this embodiment, the semitransparent surface electrode 132 of this photoelectric device covers only a fraction of the photo-active surface of the device 130. As shown in FIG. 9, the surface electrode 132 is disposed along the periphery of the ISEMCP 130, but as those skilled in the art will appreciate, the surface electrode 132 may take on other shapes covering a fraction of the photo-active surface. The photoelectric device of FIG. 9 otherwise resembles the devices discussed above in most other respects. As shown in FIG. 9, this device includes a P+ layer 135, P junction layer 133, intrinsic layer 136, N substrate layer 134, N+ layer 139, N-polysilicon layer 138, magnetically susceptible material layer 137, and posterior semitransparent surface electrode 138.

The advantage of covering a fraction of the photo-active surface, such as with the elevated rim electrode 132 shown in FIG. 9, of course, is that electrode material is eliminated from in front of the photo-active surface. Attenuation of light may still be accomplished, however, by controlling the thickness of the P junction 133. A further advantage of the embodiment shown in FIG. 9 is that less lapping is required. Only enough lapping to produce the rounded edges is needed.

Figure 10:
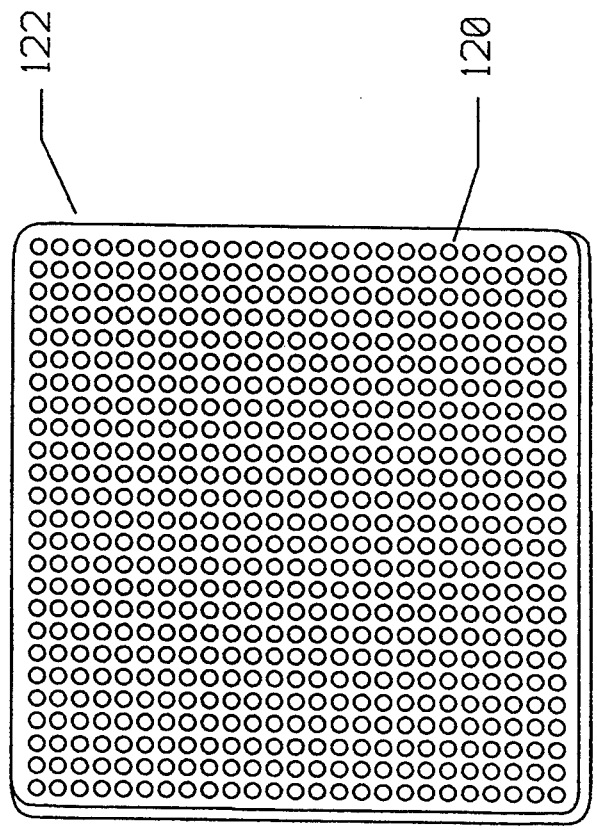
FIG. 10 is a plan view of plural ISEMCP subunits embedded in a substrate of oxygen- and nutrient-permeable, non-dissolvable or dissolvable, material.

Although the preferred method for insertion of the ISEMCP's described above involves injection of ISEMCP's suspended in a balanced salt or viscous solution, alternate forms of implantation are contemplated. For example, as shown in FIG. 10, individual ISEMCP's 120 may be embedded in a substrate sheet 122 and pre-aligned by use of a magnetic field. This sheet 122 may be cut to the dimensions of the area of retinal dysfunction by a surgeon, and implanted subretinally through a similar retinotomy incision as shown for the microsphere ISEMCP's in FIG. 5. The sheet 122 is preferably made of nutrient and oxygen permeable material, such as (but not limited to) the common materials used to fashion soft contact lenses. Such a substance could be, for example, a hydrophilic polymer of poly (2-hyroxyethylmethacrylate). An embedded two-dimensional mesh made of an inert material, such as nylon or polypropylene, may also be used to provide even separation of the ISEMCP subunits 120.

Alternatively, the ISEMCP's 120 may also be placed in a dissolvable material, such as (but not limited to) agar and collagen. Implantation of agar or collagen sheets 122, with embedded pre-aligned ISEMCP's 120, into the subretinal space would allow even separation of individual ISEMCP's 120 pre-aligned toward the incident light.

As can be seen, the photoelectric artificial retina device of the invention provides significant advantages over the prior art. The preferred ISEMCP's allow oxygen and nutrients to readily flow between the outer and inner retinal layers. Further, the individual microscopic geometries of these devices allows for accurate implantation to irregular areas of outer retinal dysfunction. Such implantation can be achieved by either injecting the ISEMCP's, which are suspended in a physiologically compatible liquid or semi-solid vehicle, into the subretinal space, or by direct implantation of ISEMCP-impregnated permeable materials.

The photoelectric devices are also substantially self-aligning, or can be aligned by application of external magnetic fields. Moreover, because the complex conversion of amplitude modulated signals to frequency modulated signals is left to intrinsic retinal mechanisms, formed vision with subretinally implanted ISEMCP's is greater than in devices that attempt to stimulate the nerve fiber layer directly with electronically constructed, frequency modulated signals.

It is to be understood that a wide range of changes and modifications to the embodiments described above will be apparent to those skilled in the art, and are also contemplated. It is therefore intended that the foregoing detailed description be regarded as illustrative rather than limiting, and that it be understood that it is the following claims, including all equivalents, that are intended to define the spirit and scope of the invention.

We claim:

1. A method of producing artificially formed vision in an eye, comprising the step of introducing a plurality of physically separate microscopic photoelectric devices into the subretinal space of the eye, wherein each of said devices ranges in size from about 0.1 to 1000 microns.

2. The method defined in claim 1, wherein said plurality of discrete microscopic photoelectric devices comprise discrete microphotodiodes.

3. The method defined in claim 2, wherein said plurality of discrete microphotodiodes comprise P-i-N semiconductors.

4. The method defined in claim 2, wherein said plurality of discrete microphotodiodes comprise N-i-P semiconductors.

5. The method defined in claim 2, further comprising the step of aligning the microphotodiodes to receive light incident upon the eye.

6. The method defined in claim 5, wherein the microphotodiodes are aligned with a magnetic field.

7. A method of producing formed vision in an eye comprising the steps of suspending a plurality of discrete microphotodiodes in a liquid, and injecting the suspension into the subretinal space of the eye, wherein at least some of the injected microphotodiodes are oriented to receive light.

8. The method defined in claim 7, wherein the plurality of microphotodiodes are introduced by a canula into the vitreous cavity for implantation into the subretinal space.

9. The method defined in claim 8, wherein the plurality of microphotodiodes are introduced into the vitreous cavity by creation of a pars plana incision.

10. The method defined in claim 9, wherein the posterior vitreous is dissected to separate the posterior hyaloid face from the retinal surface, and an incision is made through the retina.

11. The method defined in claim 10, wherein the subretinal space is entered with a small retinotomy incision along the direction of the nerve fiber layer, followed by dissection of the inner retina from the outer retina.

12. The method defined in claim 7, wherein the liquid comprises a balanced salt solution.

13. The method defined in claim 7, wherein the liquid comprises a viscous agent.

14. The method defined in claim 11, wherein the viscous agent comprises methylcellulose.

15. The method defined in claim 5, further comprising the steps of injecting a liquid that is non-miscible in water over the posterior pole in the vitreous cavity after the suspension is injected to aid in the settling of the retina, and then removing the non-miscible liquid after the retina is settled.

16. The method defined in claim 15, wherein the non-miscible liquid comprises perfluorocarbon.

17. A surgical technique for producing artificial vision comprising the steps of:
providing a pars plana incision into the eye;
providing posterior hyaloid separation of the vitreous;
creating a retinotomy opening into the retina;
dissecting and separating the retina;
suspending individual sterile microphotodiodes in an injectable vehicle; and
injecting the individual sterile microphotodiodes into the subretinal space.

18. A surgical technique for producing artificial vision comprising the steps of:
providing a pars plana incision into the eye;
providing posterior hyaloid separation of the vitreous;
creating a retinotomy opening into the retina;
dissecting and separating the retina;
embedding individual sterile microphotodiodes in a sheet wherein the sheet comprises oxygen and nutrient permeable material; and
implanting the microphotodiode-impregnated oxygen and nutrient permeable material into the subretinal space.

* * * * *